United States Patent [19]

Scortecci

[11] Patent Number: 5,312,256

[45] Date of Patent: May 17, 1994

[54] DENTAL IMPLANT FOR VERTICAL PENETRATION, ADAPTED TO DIFFERENT DEGREES OF HARDNESS OF THE BONE

[76] Inventor: Gerard Scortecci, 10, rue du Soleil, 06000 Nice, France

[21] Appl. No.: 959,621

[22] Filed: Oct. 13, 1992

[30] Foreign Application Priority Data

Oct. 10, 1991 [FR] France .................................. 91 12717

[51] Int. Cl.⁵ .............................................. A61C 8/00
[52] U.S. Cl. ...................................... 433/174; 433/173
[58] Field of Search ............... 433/172, 173, 174, 175, 433/176

[56] References Cited

U.S. PATENT DOCUMENTS

| | | | |
|---|---|---|---|
| 2,609,604 | 9/1952 | Sprague | 433/174 |
| 4,687,443 | 8/1987 | Driskell | 433/173 |
| 4,854,873 | 8/1989 | Linden | 433/173 |
| 4,932,868 | 6/1990 | Linkow et al. | 433/174 |
| 5,004,421 | 4/1991 | Lazarof | 433/173 |
| 5,061,181 | 10/1991 | Niznick | 433/174 |
| 5,076,788 | 12/1991 | Niznick | 433/173 |
| 5,194,000 | 3/1993 | Dury | 433/173 |

FOREIGN PATENT DOCUMENTS 2667499  4/1992  France .................................. 433/173

Primary Examiner—Gene Mancene
Assistant Examiner—Nicholes D. Lucchesi
Attorney, Agent, or Firm—Young & Thompson

[57] ABSTRACT

A dental implant (1) has a cylindrical body (2), with a rounded apical end (3) provided with formations (4, 5, 6, 7, 8) permitting internal bony regeneration firmly securing the implant (1). A basal end (9) forms a polygonal nut (10). The cylindrical body (2) has a succession of alternate flat parts (15, 16, 17, 18) and externally screw-threaded parts (11, 12, 13, 14), extending lengthwise of the body of the implant (1). The external threading increases the contact surface with the bone (20). The threaded parts (11, 12, 13, 14) are disposed at the periphery of circular sectors of the cylindrical body (2) and the flat parts (15, 16, 17, 18) are provided by the bottoms of longitudinal grooves. There are two wide threaded parts (11, 12) for self-tapping and/or retention in already-tapped bone (20) and two narrow threaded parts (13, 14) serving as guide rails during impacting and permitting the escape of chips during self-tapping.

7 Claims, 2 Drawing Sheets

DENTAL IMPLANT FOR VERTICAL PENETRATION, ADAPTED TO DIFFERENT DEGREES OF HARDNESS OF THE BONE

FIELD OF THE INVENTION

The invention has for its object a dental implant for vertical penetration, adapted for different degrees of hardness of the bone.

The implant according to the invention can be inserted in four different ways, as a function of the hardness of the bone.

Very dense bone: the implant according to the invention is emplaced by gentle screwing after tapping the bone.

Dense bone: the implant according to the invention is emplaced by self-tapping.

Medium dense bone: the implant according to the invention is emplaced by impact screwing.

Soft bone: the implant according to the invention is emplaced by impacting.

It is the only cylindrical and/or cylindro conical implant for axial insertion capable of possessing all of these properties, necessary in order to be emplaced according to the four modes described above, and this as a function of the hardness of the bone.

BACKGROUND OF THE INVENTION

The state of the art may be defined by the following patents:

FR-A-2,636,832: This implant is constituted by a truncated conical piece on the external surface of revolution of which is provided a conical threading and having a truncated conical axial bore opening at its large end and adapted to receive a truncated conical pivot of complementary shape secured to the prosthesis in question, means being provided for permitting the screwing of this implant into a recess first drilled and tapped in the bone of the jaw of the patient for which this prosthesis is destined.

FR-A-2,634,369: Its first element is in the shape of a spiral hollowed out by a central recess surmounted by a marginal base which positions itself at the level of the gums and whose diameter is calculated to receive both a false root and the prosthetic tooth which is supported by this latter without extending beyond said base.

FR-A-2,610,191: The intraossious implant according to the invention is constituted by a cylindrical body adapted to be emplaced in a well drilled in a bony wall after opening the soft tissues, the cylindrical body being provided with an axial recess adapted to receive a closure member after the positioning of the implant and before closing of the soft tissues and said axial recess receiving after removal of the closure member a root which carries the prosthesis. The implant according to the invention is characterized in that it is provided at the upper part of its body and in prolongation of this latter with at least one thin perforated wall.

EP-0 126 624: A fixed dental implant adapted for the jaw, comprising two connected members, one being provided with external screw threads to be screwed into the jaw and a central hole about an axis in which one end of the other part which bears a dental prosthesis is introduced. A closure is provided in the first part, the second part being introduced into the first, such that the grooves extend beyond and coact with the closure to permit a certain axial movement, as in a natural tooth. A supplemental closure is provided between the opposed surfaces of the first part and the prosthesis to give a shock absorbing effect. Hooks are provided to facilitate removal of the implant if necessary.

GB-2 210 795: The buccal implant has the shape of a cylinder comprising a flat proximal end and a rounded distal end. Projecting portions are formed on the cylindrical surface and are inclined from the proximal end of the cylindrical body toward its distal end. The projecting portions are radially spaced and grooves are provided on the inclined surface. A lateral perforation hole is provided in the distal end of the cylindrical body. The proximal end comprises a recess of hexagonal shape for the reception of a tool permitting exerting torsion.

Application to the provision of foundations for dental prostheses.

DE-U-8903050.8: Screwable implant for the securement of a dental prosthesis, with a screw-threaded portion adapted to be screwed into a jaw and with an occlusal support pillar which comprises a head, a neck as well as axially internal screw threading, characterized by the fact that the screw-threaded part is provided with a diameter regularly increasing from its free end, that between the neck and the free end, it is provided with channeling parallel to the axis, and that in the passage between the neck of generally cylindrical form and the head provided with a periphery of external polygonal shape, is provided a shoulder whose diameter is greater than that of the neck and of the head.

DE-U-9001596.7: Cylindrical self-tapping screw implant characterized by the fact that:

1. the entirely cylindrical part (about ¼ of the total length) comprises a tapped hole with an engagement chamfer and two diametrically opposed recesses for the insertion by screwing of different intrabuccal elements, or for the engagement of a tool for screwing it in 2. the entirely cylindrical part is smooth and polished and the screw element which follows it is rough or polished 3. the screw shaped part (about ¾ of the total length) as concerns the elements constituting the threading, becomes slightly thinner toward the base, but the hub, of smaller diameter, becomes thinner more abruptly 4. the end of the screw is rounded and is not self-drilling 5. the screw-shaped portion comprises two longitudinal grooves reamed also in the body of the hub, disposed obliquely relative to the longitudinal axis 6. the turns of the threading thus interrupted are sharpened at their forward end (in the direction of rotation corresponding to screwing).

The implant according to the invention is the only cylindrical and/or cylindro conical implant for axial insertion adapted to possess all of the properties necessary to be emplaced according to one or several of the four modes previously described. In other systems, only one mode is generally possible, two at the most. This is why most of the systems propose several embodiments to permit the implant to be adapted to the various categories of bone.

British patent 2 210 795 describes two types of implant: a first with the vertical striations parallel to the longitudinal axis of the implant (see FIG. 12) and a second with horizontal striations parallel to the longitudinal axis of the implant (see FIG. 1).

SUMMARY OF THE INVENTION

The implant according to the invention comprises an external threading of the helicoidal type, provided at least with a fine pitch (less than 0.50 mm) to an ultra-fine pitch of 0.25 mm, contrary to the British patent 2 210 795, which comprises several wide parallel striations that are not helicoidal. The result is that upon performing a rotation of the implant on itself, according to the major axis of the cylinder, the implant according to British 2 210 795 remains at the same level; it is incapable of advancing (the striations being parallel) while the implant according to the invention advances a distance equal to the pitch of the helix when rotated 360°.

The different degrees of hardness of the bone depend particularly on the site on the bone to be used, on the bony anatomy of the person to be treated, and on its condition.

So as to adapt it to the site on the bone to be used, the present technical literature proposes numerous specific implants. These implants are each adapted to conform specifically to different degrees of hardness of the bone and to the manner of insertion.

There can be mentioned: the hollow cylindrical implants, the hollow threaded implants, the screw implants, the implants in two parts, the impactable implants, the implants for lateral insertion with tricortical bearing, the cylindrical implants provided with an intramobile body, the cylindrical implants provided with lateral wings, the foil implants, etc...

The invention tends to simplify the work of stomatologists and dental surgeons by providing a single type of dental implant for vertical penetration rather than a difficult choice from among a multitude of implants.

The implant according to the invention also permits stomatologists and dental surgeons to adapt easily to the site upon learning the nature of the bone, while at present, in the case of a surprise, the implant must be changed because each type of implant is adapted in a specific manner to different degrees of hardness of the bone.

Of course, for a single type of implant according to the invention, there are various sizes of implant (length and diameters).

The implant according to the invention can be:
1. screwed into a very hard bone which has been first tapped, the fine pitch and the interruptions of the threading serving to reduce the internal stresses in the dense bone, which avoids the risk of necrosis.
2. screwed into a less hard bone, by self-tapping.
3. impacted in a soft bone by movement of axial translation.
4. impacted in a very soft bone, then self-tapped by a quarter turn of rotation.

To this end, the implant according to the invention is of the type comprised by a cylindrical body, with a rounded apex end provided with formations permitting a regeneration of the bone internally thereby positively securing the implant, a base end (on the summit side of the bony ridge) forming a hexagonal nut screw threaded at its center, characterized by the fact that the cylindrical body comprises a succession of planar portions and of screw-threaded portions, along all the height of the body of the implant, the external micrometric screw threading increasing the contact surface with the bone; the planar portions are micro-grooved by horizontal machining to increase as well the surface of contact; the screw-threaded portions are disposed at the periphery of circular sectors of the body of the cylinder; the planar portions are formed by the base of the longitudinally grooved section.

The apex end is rounded and smooth, and comprises a center apex opening with micrometric internal screw threading to increase the contact surface with the bony tissue and four lateral apical openings.

The cylindrical body of the implant comprises two sectors:

1. A screw-threaded sector divided in four sections: two wide sections for self-tapping and/or retention in the already tapped bone and two narrow sections serving as a guide rail during impacting.

2. A flat micro-grooved section divided in four sections by narrow screw-threaded sections. This device also permits during auto-tapping by the implant itself, to facilitate this operation by reducing the frictional forces thereby permitting a better angle of attack. Moreover, the axial grooves permit the escape of any bone chips and prevent wedging. Finally, these four planar sections interrupting the screw threading serve to block rotation once the implant is effected in the bone.

The basal end (summit side of the bony ridge) comprises a screw-threaded hexagonal nut. Said nut is micrometrically threaded, so as to permit the attachment of prosthetic parts.

BRIEF DESCRIPTION OF THE DRAWINGS

The accompanying drawings are given by way of illustrative examples and are not limiting. They show a preferred embodiment according to the invention. They will permit easy comprehension of the invention.

DETAILED DESCRIPTION OF THE INVENTION

Figure 1:
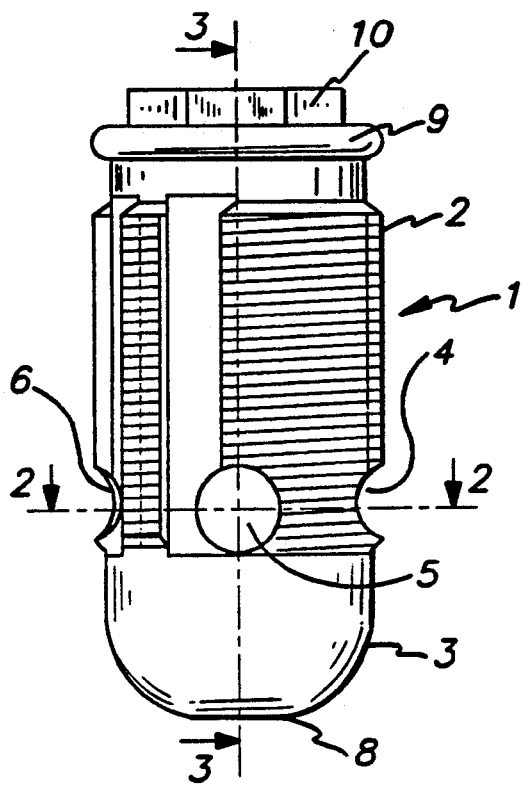
FIG. 1 is a side view of the implant according to the invention.
Figure 2:
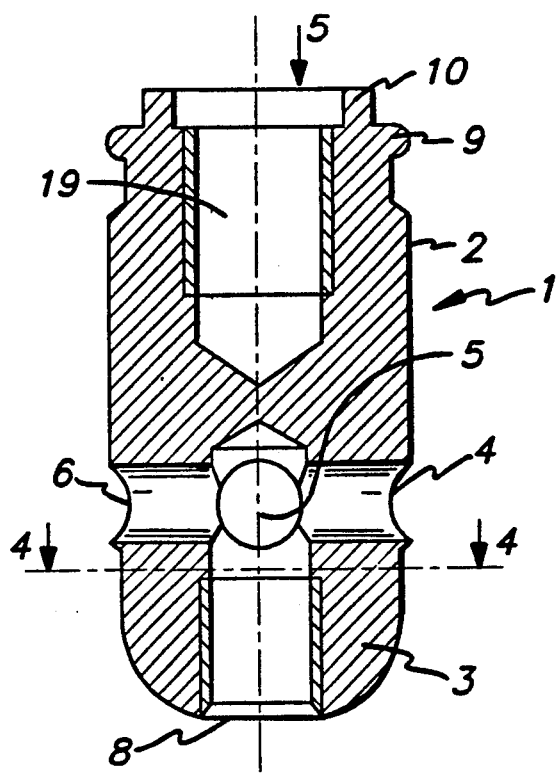
FIG. 2 is a transverse cross-sectional view on the line A—A of FIG. 1.
Figure 3:
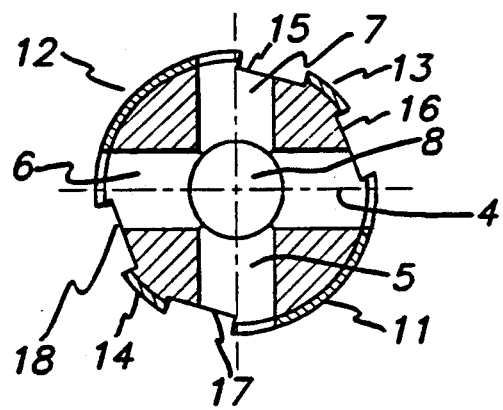
FIG. 3 is a longitudinal cross-sectional view on the line B—B in FIG. 1.
Figure 4:
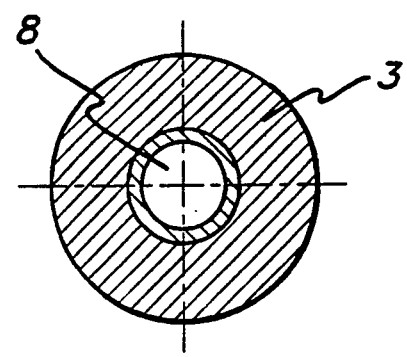
FIG. 4 is a transverse cross-sectional view at the level of the apical end, on line C—C shown in FIG. 3.
Figure 5:
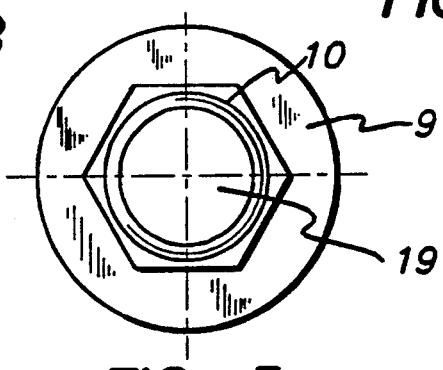
FIG. 5 is a view of the implant from the side of the end F shown in FIG. 3.
Figure 6:
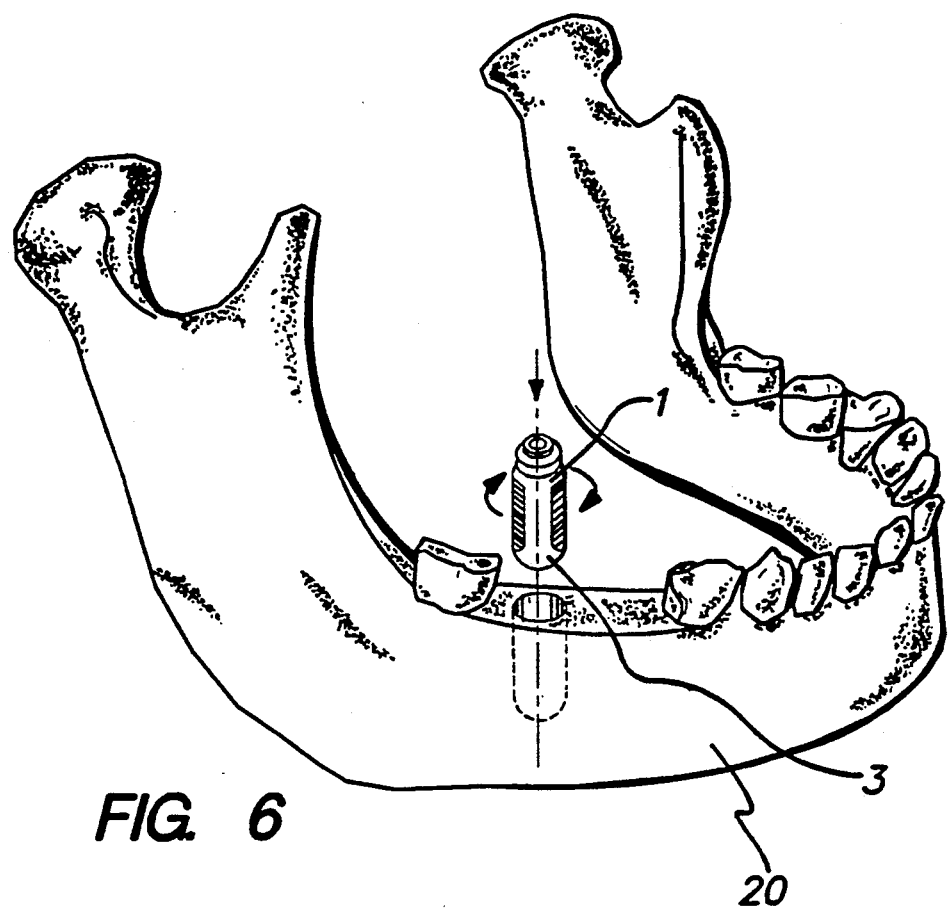
FIGS. 6 and 7 are views illustrating the emplacement of the implant in a jaw.
Figure 7:
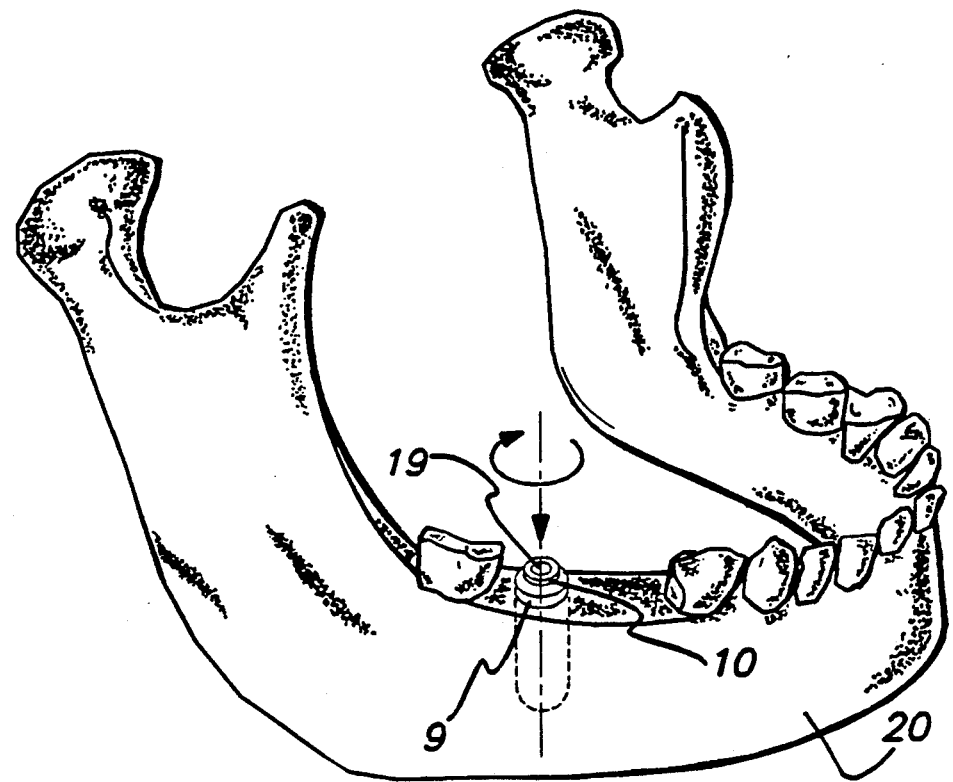

The implant 1 according to the invention is of the type comprised by a cylindrical body 2, having a rounded apex end 3, provided with openings 4, 5, 6, 7 and 8, and with a base end 9 (summit side of the bony ridge) forming a hexagonal screw-threaded nut 10.

The cylindrical body 2 comprises two sectors, a screw-threaded sector and a flat sector.

The screw-threaded sector is divided in four sections - two wide threaded sections 11, 12 for self-tapping and/or retention in the bone already tapped, and two narrow screw-threaded sections 13, 14 which serve as guide rails during impacting.

The micro-grooved flat section is divided in four sections 15, 16, 17, 18, by the screw-threaded sections.

The basal end 9 (summit side of the bony ridge) comprises a hexagonal screw-threaded nut 10, surmounting a shoulder slightly wider than the body serving as an abutment to avoid fistulation of the implant in the critical anatomical region during impacting. Said nut 10 is screw threaded at 19 micrometrically, so as to permit the connection of the prosthetic members. It is the only micrometrically internally screw-threaded implant which avoids untimely unscrewing of the prosthetic components.

The four flat sections 15, 16, 17, 18 extend over all the height of the body 2 of the implant 1 and permit impacting during dental surgery, by movement of translation. The two narrowly grooved sections 13, 14 separate the flat sections 15, 16, 17, 18 over all the height of the body 2 of the implant 1, and serve as directional stabilization rails during impacting. They permit eliminating possible chips during self-tapping. Moreover, the interruption of the screw threading on the body of the implant by means of the vertical grooves diminishes the tensile forces within the bone particularly when this latter is compact, thereby avoiding necrosis.

The succession of screw-threaded sections 11, 12, 13, 14 and flat sections 15, 16, 17, 18 permits translatory impacting with self-blocking against rotation.

Thus, if after tapping, the dental surgeon sees that the bone is too dense, he can press in the implant 1 in the axial direction. This done, the tapped portions of the bone 20 (not shown in the figures) will confront the screw-threaded sectors 11, 12, 13, 14 of the implant 1 and will be removed.

On the other hand, the portions of the bone 20 facing the four flat sections 15, 16, 17, 18 will not be removed but will remain encrusted in the vertical grooves.

Thus, these flat sections are slightly inset from the threading. It suffices at the end of impacting to subject the implant to a quarter turn, in a clockwise direction, to make the screw-threaded portion of the implant 1 coincide with the portion of the bone 20 which remains threaded in the bone and has not been smoothed during impacting. This is a technical characteristic of the implant and permits thus obtaining immediate vertical blocking of the implant 1.

Finally, the four flat sections 15, 16, 17, 18 serve also to block rotation at the end of the regrowth of the bone (about three to six months after emplacement).

The rounded apex end 3 comprises five openings 4, 5, 6, 7 and 8:

a central apical opening 8 with internal micrometric screw threading to augment the contact surface with the bony tissue 20, four openings 4, 5, 6, 7 which are in the sides of the apex.

This rounded smooth apical end:

permits the escape of fluids (blood) during emplacement of the implant and avoids any hydraulic pressure, permits intraimplant regrowth of the bone.

This apical end 3 is smooth for 2.5 mm to avoid damaging certain critical anatomical regions (sinus and/or nasal membranes, lower dental nerves, etc. . . . ) during the desired or accidental penetration of the implant.

The implant according to the invention is self-tapping, which is to say that the external screw thread is interrupted four times to leave a free space constituted by the four longitudinal vertical flat rails; this configuration of the implant body confers on the implant its self-tapping properties.

These guide rails also serve to collect fluids circulating in the spirals.

The implant is micro-threaded over all its height to increase the contact surface with the bony tissue.

This micro-threading is interrupted over all the surface in only two zones:

1. at the level of the basal end (9) (the summit side of the bony ridge):

over all the circumference of the cylinder, just above the bearing cylinder, to avoid the untimely appearance of turns at the gingival level; these turns could be the source of periodontal disease if a bony retraction were to take place 2. at the level of the apical end (3):

over about two millimeters of all the cylindro spherical surface of the apical end (3), to prevent the turns, in case of untimely penetration, in a critical anatomical non-bony region (dental canal, sinus or nasal membrane, soft tissues in the chin region) from tearing or traumatizing these tissues.

Moreover, the implant comprises a system of formations, or openings, and of channeling permitting release of the hydraulic pressure, which is a source of hypertension in the bony tissue capable of provoking cellular necrosis and loss of the implant.

Five formations or orifices are disposed at the level of the apical end:

four orifices 4, 5, 6, 7 located perpendicularly to the cylindrical surface constituted by two cylinders crossing at 90° and traversing the apex from side to side and a single cylindrical central apical orifice 8 disposed perpendicular to the two others and opening at their center.

This latter cylindrical orifice 8 is internally screw threaded, for two reasons:

1. to increase the contact surface with the bony tissue after its regrowth into the central portion of the implant 2. to permit the emplacement of an implant carrying a screw threaded pin which makes it unnecessary for the dental surgeon or his assistants to manipulate the implant with the fingers.

This perforation assembly (the two cylinders perpendicular to the implant and the central apical cylinder) open through the formations or vertical rails. They permit collecting the fluids in the apical region which are thus evacuated toward the smooth region of the basal end at which the threading ends, which is to say just below the cylinder or neck. This smooth region is the last element of the drainage system for the fluids. It plays the role of central collector by which the hydraulic pressure, the fluids, the gas and the debris are evacuated.

The implant according to the invention comprises at the level of its basal end a safety collar, or crestal bearing cylinder; this latter fulfills two roles:

1. a mechanical role:

bearing on the solid region constituted by the cortical crest, while the interior of the bone is spongy 2. safety abutment:

it avoids the untimely penetration in case of spongy bone of little density or medium density.

Thus, in the absence of this collar, the implant could in particular at the level of the sinus, be extended into an undesired anatomical region, during its emplacement. Similarly, the conjoint action of the micro-threading and the basal end abutment permits controlling very precisely the movement above the lower dental nerve.

The bearing cylinder of the basal end has a rounded (toric) cross section to avoid the effects of chiseling at the level of the bony tissue, when the implant is used.

The implant according to the invention offers the characteristic and the advantage of being already mounted on its implant carrier which is screwed in the formation or central apical orifice. Similarly, the drive system is already ready for use, mounted on the external hexagon of the implant. The surgeon need only employ directly his instruments to emplace it.

In certain favorable circumstances, the drive system may be reused as a prosthetic pillar. The implant carrier and the drive system are made of the same material as the implant itself: commercially pure titanium (greater than 99%).

What is claimed is:

1. A dental implant adapted to be anchored in a jawbone comprising a cylindrical body with a rounded apical end provided with formations permitting internal bony regeneration for firmly securing the implant, and a basal end forming a polygonal nut, wherein the cylindrical body comprises an alternating succession of flat parts and screw-threaded parts extending lengthwise of the body of the implant, said screw-threaded parts having external helicoidal threading for increasing the contact surface of the implant with the jawbone; said screw-threaded parts being disposed at the periphery of circular sectors of the cylindrical body and said flat parts being provided by the bottoms of longitudinal grooves wherein at least one of said screw-threaded parts is wide for self-tapping and/or retention in already-tapped bone and at least one of said screw-threaded parts is narrow and serves as a guide rail during impacting.

2. Implant according to claim 1, wherein the apical end is smooth and comprises a central apical orifice with internal micrometric threading for increasing the contact surface with body tissue, and four lateral apical openings.

3. Implant according to claim 2, wherein said formations comprise five openings, four of said openings being perpendicular to said cylindrical body, and crossing at 90° and traversing the apical end from side to side, and the fifth of said openings being disposed perpendicular to the other four openings, and communicating at their center.

4. Implant according to claim 1, wherein said implant includes four screw-threaded parts, two of said screw-threaded parts being wide for self-tapping and/or retention in already-tapped bone, and two of said screw-threaded parts being narrow and serving as guide rails during impacting, and permitting escape of chips during self-tapping.

5. Implant according to claim 1, wherein said nut is internally threaded, so as to permit the connection of prosthetic members, and said nut surmounts a larger neck forming an abutment.

6. Implant according to claim 1, wherein said nut surmounts an enlarged abutment, and there is a cylindrical region between said abutment and said screw-threaded parts.

7. A dental implant adapted to be anchored in a jawbone comprising a cylindrical body with a rounded apical end provided with formations permitting internal bony regeneration for firmly securing said implant, and a basal end forming a polygonal nut, wherein the cylindrical body comprising an alternating succession of flat parts and screw-threaded parts extending lengthwise of the body of the implant, said screw-threaded parts having external threading for increasing the contact surface of the implant with the jawbone; said screw-threaded parts being disposed at the periphery of circular sectors of the cylindrical body and said flat parts being provided by the bottoms of longitudinal grooves, wherein two of said screw-threaded parts are wide for self-tapping and/or retention in already-tapped bone and two of said screw-threaded parts are narrow and serve as guide rails during impacting, and permit escape of chips during self-tapping.

* * * * *